US007381528B2

(12) United States Patent
Lee et al.

(10) Patent No.: US 7,381,528 B2
(45) Date of Patent: *Jun. 3, 2008

(54) METHODS FOR DETECTION OF MUTATIONS IN MYOSTATIN VARIANTS

(75) Inventors: Se-Jin Lee, Baltimore, MD (US); Alexandra C. McPherron, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/662,003

(22) Filed: Sep. 11, 2003

(65) Prior Publication Data

US 2004/0048307 A1    Mar. 11, 2004

Related U.S. Application Data

(63) Continuation of application No. 08/967,089, filed on Nov. 10, 1997, now Pat. No. 6,673,534, which is a continuation-in-part of application No. 08/862,445, filed on May 23, 1997, now abandoned, which is a continuation-in-part of application No. 08/847,910, filed on Apr. 28, 1997, now abandoned, which is a continuation-in-part of application No. 08/795,071, filed on Feb. 5, 1997, now Pat. No. 5,994,618, which is a continuation-in-part of application No. 08/525,596, filed on Oct. 26, 1995, now Pat. No. 5,827,733.

(51) Int. Cl.
*C12Q 1/64* (2006.01)
*C12P 19/34* (2006.01)
*C07H 21/04* (2006.01)

(52) U.S. Cl. .................. 435/6; 435/91.1; 435/91.2; 536/24.3; 536/24.33

(58) Field of Classification Search ..................... None
See application file for complete search history.

(56) References Cited

U.S. PATENT DOCUMENTS

| | | | | |
|---|---|---|---|---|
| 5,585,479 A | * | 12/1996 | Hoke et al. | 536/24.5 |
| 5,756,295 A | * | 5/1998 | Onda et al. | 435/6 |
| 5,814,491 A | | 9/1998 | Vijg et al. | |
| 6,103,466 A | * | 8/2000 | Grobet et al. | 435/6 |
| 6,403,310 B1 | * | 6/2002 | Meissner et al. | 435/6 |

OTHER PUBLICATIONS

Research Genetics, "Designer PCR(TM)" (advertisement), Nucleic Acid Research, vol. 22, No. 15, Aug. 1994.*
Massague. Cell 49:437-8, 1987.*
Callard et al. The Cytokine FactsBook, Academic Press, London, pp. 31-32, 1994.*
Bowie et al. Science 247:1307-1310, 1990.*
Rudinger. Peptide Hormones, Parsons, ed., University Park Press, Baltimore, pp. 1-7, 1976.*
Wells. Biochemistry 29:8507-17, 1990.*
Ngo et al. The Protein Folding Problem and Tertiary Structure Prediction. Merz et al., eds., Birkhauser, Boston, pp. 491-495, 1994.*
Evock et al., Journal of Animal Science, vol. 66, pp. 1928-1941, Abstract only, Aug. 1988.*
Flakoll et al., Journal of Animal Science, vol. 69, pp. 1461-1467, Abstract only, Apr. 1991.*
Deli et al., Archives of Toxicology, vol. 8, pp. 277-279, Abstract only, 1985.*
Gura, Science, vol. 270, pp. 575-577, Oct. 27, 1995.*
Zhu et al., Poultry Science, vol. 74, pp. 1067-1073, Abstract only, Jul. 1995.*
Faulkner et al., Journal of Animal Science, vol. 67, pp. 1907-1915, Abstract only, Aug. 1989.*
McDowell et al., Australian Journal of Biological Sciences, vol. 40, pp. 295-306, Abstract only, 1987.*
Kappel et al., Current Opinion in Biotechnology, vol. 3, pp. 548-553, 1992.*
Strojek & Wagner, Genetic Engineering: Priniciples and Methods, vol. 10, pp. 221-246, 1988.*
Ebert et al., Molecular Endocrinology, vol. 2, pp. 277-283, 1988.*
Hammer et al., Journal of Animal Science, vol. 63, pp. 269-278, 1986.*
Moreadith et al., J. Mol. Med., vol. 75, pp. 208-216, 1997.*
Bradley et al., Biotechnology, vol. 10, pp. 534-539, May 1992.*
Seamark, Reproduction, Fertility and Development, vol. 6, pp. 653-657, 1994.*
Mullins et al., Journal of Clinical Investigation, vol. 98, pp. S37-S40, 1996.*
Wall, Theriogenology, vol. 45, pp. 57-68, 1996.*
Kambadur et al., "Mutations in myostatin (GDF8) in Double-Muscled Belgian Blue and Piedmontese Cattle," Genome Research, Sep. 1997, vol. 7, No. 9, pp. 910-916.*
Valent et al., "Nascent membrane and presecretory proteins synthesized in *Escherichia coli* associate with signal recognition particle and trigger factor," Molecular Microbiology, Jul. 1997, vol. 25, No. 1, pp. 53-64.*
McDowell et al. Effects of Exogenous Growth Hormone on Milk Production and Nutrient Uptake by Muscle and Mammary Tissues of Dairy Cows in Mid-Lactation. Australian Journal of Biological Sciences, vol. 40, No. 3, pp. 295-306, see Abstract, 1989.
Evock et al. Pituitary Porcine Growth Hormone (pGH) and a Recombinant pGH Analog Stimulate Pig Growth Performance in a Similar Manner. Journal of Animal Science, vol. 66, No. 8, pp. 1928-1941, see Abstract, 1988.
Flakoll et al. Influence of Alpha-Ketoisocaproate on Lamb Growth, Feed, Conversion, and Carcass Composition. Journal of Animal Science, vol. 69, No. 4, pp. 1461-1467, see Abstract, 1991.
Deli et al. Biochemical Study of Muscle Samples from Chicken Embryos Affected by Wofatox 50 EC. Archives of Toxicology, vol. 8, pp. 277-279, see Abstract, 1985.

(Continued)

*Primary Examiner*—Young J. Kim
(74) *Attorney, Agent, or Firm*—DLA Piper US LLP

(57) ABSTRACT

Methods for detecting allelic variants of the myostatin (growth and differentiation factor-8) gene are provided. Specifically provided are methods of identifying subjects having or having a predisposition for increased muscle mass as compared to subjects having wild-type myostatin. Increased muscle mass is particularly desirable for identification of animals used to produce food products, including bovine, porcine, ovine, avian and piscine species.

28 Claims, 2 Drawing Sheets

OTHER PUBLICATIONS

Faulkner et al. Effect of Testosterone Propionate on Performance and Carcass Characteristics of Heifers and Cows. Journal of Animal Science, vol. 67, No. 8, pp. 1907-1915, see Abstract, 1989.

Zhu et al. Survey of Major Histocompatibility Complex Class II Haplotypes in Four Turkey Lines Using Restriction Fragment Length Polymorphism Analysis with Nonradioactive DNA Detection. Poultry Science, vol. 74, No. 7, pp. 1067-1073, see Abstract 1989.

Bowie et al., "Deciphering the Message in Protein Sequences: Tolerance to Amino Acid Substitutions", *Science*, 247:1307-1310, 1990.

Rudlinger, "Characteristics of the amino acids as components of peptide hormone sequence", *Peptide Hormones. Parsons Ed ..*, University Park Press, Baltimore, pp. 1-7 1976.

Wells, "Additivity of Mutational Effects in Proteins", *Biochemistry*, 29:8507-17 1990.

Ngo et al., "The Computational Complexity, Protein Structure Prediction, andthe Levinthal Paradox", *The Protein Folding Problem and Tertiary Structure Prediction*, Mertz et al., eds., Birkhauser, Boston, pp. 491-495, 1994.

Massague, "The TGF-β Family of Growth and Differentiation Factors", *Cell*. 49:437-38, 1987.

Callard et al., "IL-1", *The Cytokine FactsBook*, Academic Press, London, pp. 31-32, 1994.

McPherron et al., "GDF-3 and GDF-9: Two New Members of the Transforming Growth Factor-β Superfamily Containing a Novel Pattern of Cysteines", *The Jounral of Biological Chemistry*, 268(5):3444-49 (1993).

Lee, "Expression of growth/differentiation factor 1 in the nervous system: Conservation of a bicistronic structure", *Proc. Natl. Acad. Sci.* USA, 88:4250-54 (1991).

Lee, "Identification of a Novel Member (GDF-1) of the Transforming Growth Factor-β Superfamily", *Molecular Endocrinology*, 4(7):1034-39 (1990).

Kambadur, et al.; "Mutations in *myostatin* (*GDF8*) in Double-Muscled Belgian Blue and Piedmontese Cattle"; Genome Research, 7:910-915 © 1997 by Cold Spring Harbor Laboratory Press.

Dickman, Steven; "Gene Mutation Provides More Meat on the Hoof"; Science, vol. 277, Sep. 26, 1997, pp. 1922-1923.

Westhusin, Mark; "From mighty mice to mighty cows"; Nature Genetics, vol. 17, Sep. 1997, pp. 4-5.

Grobet, et al.; "A deletion in the bovine myostatin gene causes the double-muscled phenotype in cattle"; Nature Genetics, vol. 17, Sep. 1997, pp. 71-74.

\* cited by examiner

```
                          SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: Oligonucleotides (xi) SEQUENCE DESCRIPTION: SEQ ID NO: 1:

GATCCCAAAA CACTCTCCTA CCTCGGATCC GCG                                    33

(2) INFORMATION FOR SEQ ID NO: 2:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: Oligonucleotides (xi) SEQUENCE DESCRIPTION: SEQ ID NO: 2:

CCCCTCAACA ATTTTGAAAC TGTGGGATCC GCG                                    33

(2) INFORMATION FOR SEQ ID NO: 3:

(i) SEQUENCE CHARACTERISTICS:
          (A) LENGTH: 33 base pairs
          (B) TYPE: nucleic acid
          (C) STRANDEDNESS: single
```

(D) TOPOLOGY: linear (ii) MOLECULE TYPE: Oligonucleotides (xi) SEQUENCE DESCRIPTION: SEQ ID NO: 3:

CGCGGATCCG AGGTAGGAGA GTGTTTTGGG ATC                                33

(2) INFORMATION FOR SEQ ID NO: 4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Oligonucleotides (xi) SEQUENCE DESCRIPTION: SEQ ID NO: 4:

CGCGGATCCC ACAGTTTCAA AATTGTTGAG GGG                                33

(2) INFORMATION FOR SEQ ID NO: 5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotides (xi) SEQUENCE DESCRIPTION: SEQ ID NO: 5:

GTGGAGTGTT CAT                                                     13

(2) INFORMATION FOR SEQ ID NO: 6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotides (xi) SEQUENCE DESCRIPTION: SEQ ID NO: 6:

GATTCTGTCA CAA                                                     13

(2) INFORMATION FOR SEQ ID NO: 7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotides (xi) SEQUENCE DESCRIPTION: SEQ ID NO: 7:

AATTCACATT CTC                                                     13

(2) INFORMATION FOR SEQ ID NO: 8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotides -continued (xi) SEQUENCE DESCRIPTION: SEQ ID NO: 8:

AATTCATATT CTC                                                      13

(2) INFORMATION FOR SEQ ID NO: 9:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotides (xi) SEQUENCE DESCRIPTION: SEQ ID NO: 9:

ATGAACACTC CAC                                                      13

(2) INFORMATION FOR SEQ ID NO: 10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotides (xi) SEQUENCE DESCRIPTION: SEQ ID NO: 10:

TTGTGACAGA ATC                                                      13

(2) INFORMATION FOR SEQ ID NO: 11:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Oligonucleotides (xi) SEQUENCE DESCRIPTION: SEQ ID NO: 11:

GAGAATGTGA ATT                                                      13

(2) INFORMATION FOR SEQ ID NO: 12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GAGAATATGA ATT                                                      13

METHODS FOR DETECTION OF MUTATIONS IN MYOSTATIN VARIANTS

This application is a continuation application of U.S. patent application Ser. No. 08/1,967,089 filed November 10, 1997, now U.S. Pat. No. 6,673,534 now pending, which is a continuation-in-part of U.S. patent application Serial No. 08/862,445 filed May 23, 1997, now abandoned; which is a continuation-in-part of U.S. patent application Ser. No. 08/847,910 filed Apr. 28, 1997, now abandoned; which is a continuation-in-part of U.S. patent application Ser. No. 08/795,071 filed Feb. 5, 1997, now issued as U.S. Pat. No. 5,994,618; which is a continuation-in-part of U.S. patent application Ser. No. 08/525,596 filed Oct. 26, 1995, now issued as U.S. patent 5,827,733. The disclosure of each of the prior applications is considered part of and is incorporated by reference in the disclosure of this application.

TECHNICAL FIELD

The present invention relates generally to growth factors and more specifically to methods for detecting variants of myostatin, previously known as growth differentiation factor-8 (GDF-8), in a specimen.

BACKGROUND

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., *Nature*, 345:167, 1990), Drosophila decapentaplegic (DPP) gene product, which is required for dorsal-ventral axis formation and morphogenesis of the imaginal disks (Padgett, et al., *Nature*, 325:81-84, 1987), the Xenopus Vg-1 gene product, which localizes to the vegetal pole of eggs (Weeks, et al., *Cell*, 51:861-867, 1987), the activins (Mason, et al., *Biochem, Biophys. Res. Commun.*, 135:957-964, 1986), which can induce the formation of mesoderm and anterior structures in Xenopus embryos (Thomsen, et al., *Cell*, 63:485, 1990), and the bone morphogenetic proteins (BMPs, osteogenin, OP-1) which can induce de novo cartilage and bone formation (Sampath, et al., *J. Biol. Chem.*, 265:13198, 1990). The TGF-βs can influence a variety of differentiation processes, including adipogenesis, myogenesis, chondrogenesis, hematopoiesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110-140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A. et al., *Science*, 247:1328, 1990). Additional studies by Hammonds, et al., (*Molec. Endocrin.* 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., *Nature*, 321:779, 1986) and the TGF-βs (Cheifetz, et al., *Cell*, 48:409, 1987), heterodimers have also been detected, and these appear to have different biological properties than the respective homodimers.

A member of the TGF-β superfamily, originally termed growth and differentiation factor-8 (GDF-8), now known as myostatin, was recently identified as being expressed in developing and adult skeletal muscle tissue (McPherron, A. C., Lawler, A. M. & Lee, S-J. (1997) *Nature* 387: 83). Myostatin null mice show a dramatic and widespread increase in skeletal muscle mass. Individual muscles in myostatin null mice weigh 2- to 3-fold more than those of wild-type mice, primarily due to an increased number of muscle fibers without a corresponding increase in the amount of fat. Thus, the myostatin gene product acts as a negative regulator of skeletal muscle development in mice.

It is desirable to produce livestock and game animals, such as cows, sheep, pigs, chicken, turkey and fish which are relatively high in musculature and/or low in fat content. Many drug and diet regimens exist which may help increase muscle and protein content and lower undesirably high fat and/or cholesterol levels, but such treatment is generally administered after the fact, and is begun only after significant damage has occurred to the vasculature. Accordingly, it would be desirable to identify animals which are genetically predisposed to having higher muscle content, without any ancillary increase in fat levels.

The food industry has put much effort into increasing the amount of muscle and protein in foodstuffs. This quest is relatively simple in the manufacture of synthetic foodstuffs, but has been met with limited success in the preparation of animal foodstuffs. Attempts have been made, for example, to lower cholesterol levels in beef and poultry products by including cholesterol-lowering drugs in animal feed (see e.g. Elkin and Rogler, *J. Agric. Food Chem.*, 38:1635).

SUMMARY OF THE INVENTION

The present invention provides a method for detecting variants in the myostatin gene which influence hypertrophic and hyperplastic muscle development. The present method allows for the identification of subjects having an altered myostatin gene as compared to the wild-type myostatin gene.

The present invention provides a method for detecting the presence of a myostatin variant nucleotide sequence in a subject having, or predisposed to having, increased muscle mass. The invention also provides oligonucleotide probes and target sequences for the identification of myostatin allelic variants.

The subject invention also provides a kit containing oligonucleotides necessary to detect the presence of myostatin genetic variants. Such kits are useful for detecting myostatin variants for the purpose of identifying those subjects having or predisposed to having increased muscle mass.

In another embodiment, the invention provides a method for detecting the presence of a myostatin variant protein. The invention also provides a kit containing antibodies useful for the detection of such variants. The antibodies can be used, for example, to distinguish a myostatin variant from the wild-type protein by detecting a difference in the size of the variant as compared to wild-type myostatin protein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The TGF-β superfamily consists of multifunctional polypeptides that control proliferation, differentiation, and other functions in many cell types. Many of the polypeptides have regulatory, both positive and negative, effects on other growth factors. The myostatin protein is a member of the TGF-β family and is believed to play a role in the regulation of muscle development myostatin null mice show a dramatic and widespread increase in skeletal muscle mass. Individual muscles in myostatin null mice weigh 2- to 3-fold more than those of wild-type mice. These data indicate that myostatin possesses biological activities which make it a useful target in identifying subjects having or predisposed to having increased muscle mass development.

Figure 1A:
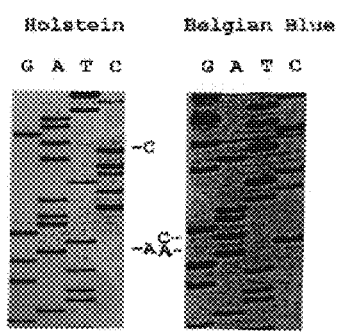
FIG. 1A shows a sequencing gel of myostatin mutations in Belgian Blue cattle compared to wild-type Holstein cattle. The nucleotides immediately preceding (A936) and following (C937) the Belgian Blue 11 nucleotide deletion are indicated.
Figure 1B:
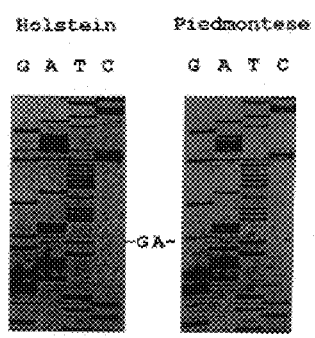
FIG. 1B shows a sequencing gel of myostatin mutations in Piedmontese cattle compared to wild-type Holstein cattle.

The present invention shows that deletion of nucleotides 937-947, in the third exon of the myostatin gene, is found in nucleic acid isolated from Belgian Blue cattle (FIG. 1B). This 11 nucleotide deletion causes a frame-shift that is predicted to result in a truncated protein that terminates 14 codons downstream of the site of the mutation. The deletion is expected to be a null mutation since it occurs after only the first 7 amino acids of the C-terminal region resulting in a loss of 102 amino acids (amino acids 274-375). Further, the present invention shows the identification of a myostatin sequence variant in Piedmontese cattle. The variant myostatin sequence contains a G to A transition in exon 3 resulting in a cysteine to tyrosine substitution in the mature region of the protein (amino acid 313) (FIG. 1B). This mutation is likely to result in a complete or almost complete loss of function as this cysteine residue is invariant not only among all myostatin sequences but also among all known members of the TGF-β superfamily.

The present invention provides a method for identifying genetic variants of myostatin. The method of the invention is based on the discovery that the myostatin gene is highly conserved among vertebrate species and that two breeds of cattle, characterized as having increased muscle mass (i.e., double muscling), have mutations in the myostatin coding sequence. The two breeds of cattle, Belgian Blue and Piedmontese, display a 20-25% increase in muscle mass as compared to conventional cattle. These results demonstrate that the function of myostatin has been highly conserved among vertebrates and indicates that the identification of a myostatin variant is predictive of the double muscling phenotype. Thus, methods for identifying such variants are useful, for example, in screening livestock and game animals, such as cows, sheep, pigs, chicken, turkey and fish, to predict which animals will display the double muscling phenotype. Accordingly, the present invention can be used to identify animals which are genetically predisposed to having increased muscle mass or which presently have increased muscle mass.

In a preferred embodiment, the present invention provides a method for detecting the presence of a target myostatin variant nucleic acid sequence in a nucleic acid-containing specimen wherein the specimen is isolated from a subject having increased muscle mass as compared to a subject having a wild-type nucleic acid sequence or having a predisposition for increased muscle mass. The method includes isolating nucleic acid present in the specimen and detecting the presence of the target myostatin variant nucleic acid sequence, wherein the presence of the variant target nucleotide sequence is indicative of a predisposition for increased muscle mass or the presence of increased muscle mass.

"Nucleic acid sequence" as used herein, refers to an oligonucleotide, nucleotide or polynucleotide, and fragments or portions thereof, and to DNA or RNA of genomic or synthetic origin which can be single- or double-stranded, and represent the sense or antisense strand.

"Variant" as used herein, refers to any myostatin nucleic acid sequence which does not correspond to the wild-type myostatin nucleic acid sequence as well as the corresponding amino acid sequence. The method of the invention includes variants of segments of myostatin which do not share sequence identity with the corresponding segment of the wild-type myostatin sequence. The following myostatin wild-type nucleic acid sequences have been reported to the GenBank database: baboon (accession no. AFO19619), bovine (accession no. AFO19620), chicken (accession no. AFO19621), ovine (accession no. AFO19622), porcine (accession no. AFO19623), rat (accession no. AFO19624), turkey (accession no. AFO19625), zebrafish (accession no. AFO19626) and human (accession no. AFO19627).

The illustrative example using the method of the invention was used to identify myostatin variants in Belgian Blue and Piedmontese cattle. For example, a deletion of nucleotides 937-947 occurs in the third exon of the myostatin gene isolated from Belgian Blue cattle (FIG. 1B). Further, in Piedmontese cattle, the variant myostatin sequence contains a G to A transition in exon 3 resulting in a cysteine to tyrosine substitution at amino acid 313 (FIG. 1B). Though the present invention was used to identify these particular variants, it is understood that the method of the invention is not limited to these examples. It is envisioned the present method can be used to identify myostatin variants in other subjects including transgenic non-human animals.

The "transgenic non-human animals" and other subjects of the invention include bovine, porcine, ovine, avian and piscine (e.g., cow, pig, sheep, chicken, turkey, fish). Transgenic animals are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., *Proc. Natl. Acad. Sci. USA* 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Variants of the invention can be generated by a mutation, a restriction fragment length polymorphism, a nucleic acid deletion, or a nucleic acid substitution naturally occurring or intentionally manipulated. A "restriction fragment length polymorphism" results from a loss or creation of a site at which a particular restriction enzyme cuts in a nucleotide sequence. Polynucleotides encoding different allelic forms will give different sizes of polynucleotide fragments on digestion with the appropriate restriction enzyme. A "deletion" is defined as a change in the nucleotide sequence in which one or more nucleotide residues are absent. A "substitution" results from the replacement of one or more nucleotide residues with non-identical nucleotide residues.

Variants also include peptides, or full length protein, that contains substitutions, deletions, or insertions into the protein backbone, that would still leave a 70% homology to the original protein over the corresponding portion. A yet greater degree of departure from homology is allowed if like-amino acids, i.e. conservative amino acid substitutions, do not count as a change in the sequence. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, for example of possible modifications. The modified peptides can be chemically synthesized, or the isolated gene can be site-directed mutagenized, or a synthetic gene can be synthesized and expressed in bacteria, yeast, baculovirus, tissue culture and so on.

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular variant can easily be made by one skilled in the art based on practical considerations: size of the desired peptide, availability and cost of starting materials, etc. All the technologies involved are well established and well known in the art. See, for example, Ausubel et al., CURRENT PROTOCOLS IN MOLECULAR BIOLOGY, Volumes 1 and 2 (1987), with supplements, and Maniatis et al., MOLECULAR CLONING, A LABORATORY MANUAL, Cold Spring Harbor Laboratory (1989). Yet other technical references are known and easily accessible to one skilled in the art.

The term "isolated" as used herein includes polynucleotides substantially free of other nucleic acids, proteins, lipids, carbohydrates or other materials with which it is naturally associated. Polynucleotide sequences of the invention include DNA and RNA sequences which encode myostatin variants. It is understood that all polynucleotides encoding all or a portion of myostatin variants are also included herein. Such polynucleotides include naturally occurring, synthetic, and intentionally manipulated polynucleotides. The polynucleotides of the invention include sequences that are degenerate as a result of the genetic code. A complementary sequence may include an antisense nucleotide. When the sequence is RNA, the deoxyribonucleotides A, G, C, and T are replaced by ribonucleotides A, G, C, and U, respectively. Also included in the invention are fragments (portions) of the above-described nucleic acid sequences that are at least 10-15 bases in length, which is sufficient to permit the fragment to specifically hybridize to DNA of the variant myostatin nucleic acid.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Nucleic acid sequences of the invention can be obtained by several methods. For example, DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

The development of specific DNA sequences encoding GDF-8, or variants thereof, can also be obtained by: 1) isolation of double-stranded DNA sequences from the genomic DNA; 2) chemical manufacture of a DNA sequence to provide the necessary codons for the polypeptide of interest; and 3) in vitro synthesis of a double stranded DNA sequence by reverse transcription of mRNA isolated from a eukaryotic donor cell. In the latter case, a double-stranded DNA complement of mRNA is eventually formed which is generally referred to as cDNA.

Allelic Variants

The method of the invention includes identifying allelic variants in a subject. The subject may be homozygous or heterozygous for a myostatin variant. As used herein, an "allele" is a gene present in more than one form (different sequence) in a genome. "Homozygous", according to the present invention, indicates that the myostatin gene is present as two copies (i.e., alleles), each allele being identical in sequence and function to the other allele. For example, a subject homozygous for the wild-type myostatin gene contains at least two copies of the myostatin wild-type sequence. Such a subject would not be predisposed to an increase in muscle mass and, therefore, would not exhibit the "double-muscling" phenotype. In contrast, a subject homozygous for a variant myostatin gene, such as, for example, the myostatin of the invention contained in Belgian Blue cattle, contains at least two copies of variant alleles of the myostatin gene and would exhibit the double-muscling phenotype or at least be predisposed to the phenotype.

"Heterozygous" as used in the present invention, indicates that one copy of the wild-type allele and one copy of the variant allele are present in the genome. A subject having such a genome is heterozygous. A heterozygote of the present invention exhibits an intermediate increase in muscle mass as compared to the homozygote wild-type myostatin. In other words, partial loss of function of myostatin leads to a partial increase in muscle mass. One of skill in the art would readily be able to determine if a particular mutation was able to partially inhibit myostatin expression or function, thus resulting in increased muscle mass. For example, in vitro testing may be desirable initially by comparison with wild-type myostatin (e.g., comparison of Northern blots to detect a decrease in expression). Heterozygous, as used in the present invention, also encompasses a subject having two different mutations in myostatin alleles. For example, a cross between Belgian Blue and Piedmontese cattle, both of which are homozygous for different myostatin variants, would result in offspring which are heterozygous for two different myostatin variants. Such an animal may have, for example, an eleven base-pair deletion in one myostatin allele and a G to A substitution mutation in the second myostatin allele. In this example, the animal heterozygous for two myostatin variants would exhibit a double-muscling phenotype similar to that of an animal homozygous for either of the mutations.

Thus, it is envisioned that the method of the invention is useful for developing an allelic profile of a subject for the myostatin gene. "Allelic profile", as used herein, is a determination of the composition of a subject's genome in regard to the presence or absence, and the copy number, of the myostatin allele or variants thereof.

In a preferred embodiment, the invention provides a method of determining predisposition of a subject to increased muscle mass. The method includes determining the myostatin allelic profile of a subject by isolating the nucleic acid specimen from the subject which includes the myostatin sequence and determining the presence or absence of a mutation in the myostatin nucleic acid sequence. The invention also provides a diagnostic or prognostic method for determining the myostatin allelic profile of a subject including isolating a nucleic acid sample from the subject; amplifying the nucleic acid with primers which hybridize to target sequences.

Several methods are available for detection of allelic variants in myostatin. For example, allele specific oligonucleotides (ASO's) can be used as probes to identify such variants. ASO probes can be any length suitable for detecting the sequence of interest. Preferably such probes are 10-50 nucleotides in length and will be detectably labeled by isotopic or nonisotopic methods. The target sequences can be optionally amplified and separated by gel electrophoresis prior to immobilization by Southern blotting. Alternatively, extracts containing unamplified nucleic acid can be transferred to nitrocellulose and probed directly as dot blots.

An alternative to the dot-blot method is the reverse dot blot method in which the ASO's are immobilized on to a membrane, which is then hybridized with target sequences that have been labelled during amplification.

In addition, allele-specific alterations can be identified by coincidental restriction site alteration. Mutations sometimes alter restriction enzyme cleavage sites or, alternatively, introduce restriction sites were none had previously existed. The change or addition of a restriction enzyme recognition site can be used to identify a particular myostatin variant.

Allele-specific amplification and allele-specific ligation, utilizing oligonucleotides complementary to either the wild-type or the variant sequence, are included in the present invention as methods for identifying specific mutations. For example, oligonucleotides can be designed such that they specifically hybridize to a wild-type or variant nucleotide sequence in a myostatin polynucleotide. The oligonucleotides support amplification or ligation only when hybridized to the appropriate complementary sequence.

Amplification of Target Sequences

When it is desirable to amplify the target nucleic acid sequence before detection, such as a myostatin nucleic acid sequence, this can be accomplished using oligonucleotide(s) that are primers for amplification. These oligonucleotide primers are based upon identification of the flanking regions contiguous with the target nucleotide sequence. For example, in the case of myostatin, these oligonucleotide primers comprise sequences which hybridize with nucle otide sequences flanking myostatin exon 3. Exemplary target sequences include the following nucleotide sequences:

```
                                                 (SEQ ID NO:1)
    5'-GATCCCAAAACACTCTCCTACCTCGGATCCGCG-3'; and (SEQ ID NO:2)
    5'-CCCCTCAACAATTTTGAAACTGTGGGATCCGCG-3', and
``` sequences complementary thereto. Exemplary oligonucleotides which hybridize to such sequences include:

```
                                                 (SEQ ID NO:3)
    5'-CGCGGATCCGAGGTAGGAGAGTGTTTTGGGATC-3'; and (SEQ ID NO:4)
    5'-CGCGGATCCCACAGTTTCAAAATTGTTGAGGGG-3'.
```

One skilled in the art will be able to generate oligonucleotide primers suitable for amplifying target sequences of additional genes, such as those flanking loci of other myostatin variants, using routine skills known in the art and the teachings of this invention.

In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15-22 or more nucleotides, although it may contain fewer nucleotides as long as the primer is of sufficient specificity to allow essentially only the amplification of the specifically desired target nucleotide sequence (i.e., the primer is substantially complementary).

Experimental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be "substantially" complementary to each strand of mutant nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the mutant nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized +and − strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphos-phoramidites are used as starting materials and may be synthesized as described by Beaucage, et al. (*Tetrahedron Letters*, 22:1859-1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

The nucleic acid from any tissue specimen, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified may be a fraction of a larger molecule or can be present initially as a discrete molecule, such that the specific sequence constitutes the entire nucleic acid. It is not necessary that the sequence to be amplified be present initially in a pure form; it may be a minor fraction of a complex mixture, such as contained in whole human or animal DNA.

Where the target variant nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP which is known to denature DNA. The reaction conditions suitable for strand separation of nucleic acids with helicases are described by Kuhn Hoffmann-Berfing (*CSH-Quantitative Biology,* 43:63, 1978) and techniques for using RecA are reviewed in C. Radding (*Ann. Rev. Genetics,* 16:405-437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates. Generally synthesis occurs in a buffered aqueous solution, preferably at a pH of 7-9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C.

The agent for polymerization may be any compound or system which will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerase, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by Southern blot analysis, without using radioactive probes. In such a process, for example, a small sample of DNA containing a very low level of mutant nucleotide sequence is amplified, and analyzed via a Southern blotting technique. The use of non-radioactive probes or labels is facilitated by the high level of the amplified signal.

Screening for Target Sequences

The variant GDF-8 nucleic acid sequence of the invention can be derived from any organism or subject including mouse, rat, cow, pig, human, horse, sheep, goat, chicken, turkey, fish and other species are also included herein. Examples of specimens from which nucleic acid sequence can be derived include food products derived from avian, bovine, ovine, piscine, murine and porcine species. Screening procedures which rely on nucleic acid hybridization make it possible to isolate any gene sequence from any organism, provided the appropriate probe is available. Given the extensive nucleotide and amino acid homology between species, it would be routine for one of skill in the art to obtain polynucleotides encoding myostatin from any species. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

In an embodiment of the invention, purified nucleic acid fragments containing intervening sequences or oligonucleotide sequences of 10-50 base pairs are radioactively labeled. The labeled preparations are used to probe nucleic acid from a specimen by the Southern hybridization technique. Nucleotide fragments from a histologic specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72-81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an subject having or predisposed to having increased muscle mass. Thus, in a preferred embodiment where the variant nucleotide sequence to be detected is myostatin, a hybridization probe is utilized which is capable of hybridizing with nucleotide sequences comprising:

```
5'-GTGGAGTGTTCAT-3'  (SEQ ID NO:5);

5'-GATTCTGTCACAA-3'  (SEQ ID NO:6);

5'-AATTCACATTCTC-3'  (SEQ ID NO:7); or

5'-AATTCATATTCTC-3'  (SEQ ID NO:8)
``` and sequences complementary thereto. Exemplary oligonucleotide probes which hybridize to the target nucleic acid sequence include:

```
5'-ATGAACACTCCAC-3'  (SEQ ID NO:9);

5'-TTGTGACAGAATC-3'  (SEQ ID NO:10);
```

-continued
```
5'-GAGAATGTGAATT-3'  (SEQ ID NO:11); or

5'-GAGAATATGAATT-3'  (SEQ ID NO:12)
``` and sequences complementary thereto.

For the most part, the probe will be detectably labeled with an atom or inorganic radical, most commonly using radionuclides, but also heavy metals can be used. Conveniently, a radioactive label may be employed. Radioactive labels include $^{32}$P, $^{125}$I, $^{3}$H, $^{14}$C, $^{111}$In, $^{99m}$Tc, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}$P-dNTP or terminal phosphate hydrolysis with alkaline phosphatase followed by labeling with radioactive $^{32}$P employing $^{32}$P-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}$P phosphate, or $^{14}$C organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a specimen can be cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300-500 kD), polyvinylpyrrolidone, (about 250-500 kD) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, (*Proc. Natl. Acad. Sci.* 63:378, 1969); and John, et al., (*Nature,* 223:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific fluorescent antibody. Horseradish peroxidase enzyme can be conjugated to the antibody to catalyze a chemiluminescent reaction. Production of light can then be seen on rapid exposure to film.

Nucleic acids having a myostatin variant detected by the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008-1012, 1985), allele-specific oligonucleotide (ASO) probe analysis (Conner, et al., *Proc. Natl. Acad. Sci. USA,* 80:278, 1983), oligonucleotide ligation assays (OLAs) (Landegren, et al., *Science,* 241:1077, 1988), and the like. Molecular techniques for DNA analysis have been reviewed (Landegren, et al., *Science,* 242:229-237, 1988).

Detection of Myostatin Protein Variants

According to another embodiment of the invention, anti-wt myostatin specific monoclonal antibodies and anti-myostatin variant specific monoclonal antibodies can be used to determine the myostatin allelic profile of a subject indirectly. According to the embodiment, antibodies are produced which bind to an epitope of wt myostatin and the antibodies are labeled as described below. Protein extracts from a subject are exposed separately to each of the two types of antibodies e.g., monoclonals. The results identify and distinguish a subject that is homozygous (wt/wt or variant/ variant) or heterozygous (wt/variant or variant$^1$/variant$^2$) for myostatin and identifies which of the alleles is present. For example, if in separate testing of aliquots of an extract employing anti-wt or anti-myostatin variant, both antibodies indicate presence of substrate, the heterozygote allelic condition is identified. Methods for producing antibodies to wt myostatin protein and variants thereof are discussed below and are well known in the art.

As used in this invention, the term "epitope" refers to an antigenic determinant on an antigen, such as a myostatin polypeptide, to which the paratope of an antibody, such as an myostatin-specific antibody, binds. Antigenic determinants usually consist of chemically active surface groupings of molecules, such as amino acids or sugar side chains, and can have specific three-dimensional structural characteristics, as well as specific charge characteristics.

Preparation of an antibody requires a substantially purified moiety that can provide an antigenic determinant. The term "substantially pure" as used herein refers to GDF-8, or variants thereof, which is substantially free of other proteins, lipids, carbohydrates or other materials with which it is naturally associated. Substantially purified or "isolated" refers to molecules, either nucleic or amino acid sequences, that are removed from their natural environment, isolated or separated, and are at least 60% free, preferably 75% free, and most preferably 90% free from other components with which they are naturally associated. One skilled in the art can isolate GDF-8 using standard techniques for protein purification. The substantially pure polypeptide will yield a single major band on a non-reducing polyacrylamide gel. The purity of the GDF-8 polypeptide can also be determined by amino-terminal amino acid sequence analysis. GDF-8 polypeptide includes functional fragments of the polypeptide, as long as the activity of GDF-8 remains. Smaller peptides containing the biological activity of GDF-8 are included in the invention. As used in the present invention, the term "antibody" includes, in addition to conventional antibodies, such protein fragments that have the ability to recognize specifically and bind the myostatin protein or variants thereof. For example, in the present invention, the gene sequence of myostatin and myostatin variants are known. Regions of the gene that differ at the protein level are well defined. A protein can be raised by expression of the wt gene or of the variants, or, preferably, fractions therefore. For example, the nucleic acid sequence can be cloned into expression vectors. According to this embodiment, the sequence of interest can first be obtained by employing PCR, as described above, or from a synthetic gene construction with overlapping and ligated synthetic oligonucleotides. Another alternative would involve synthesis of a short peptide. All those methodologies are well known to one skilled in the art. See, for example, Ausubel et al., CURRENT PROTOCOLS IN MOLECULAR BIOLOGY, Volumes 1 and 2 (1987), with supplements, and Maniatis et al., MOLECULAR CLONING, A LABORATORY MANUAL, Cold Spring Harbor Laboratory.

The genetic sequence discussed above then is expressed in any known, commercially available systems. Vectors for subcloning the sequence of interest, and subsequent expression into bacterial, yeast, baculovirus, insect, or tissue culture are well known to one skilled in the art. The subcloning process could, according to one embodiment, produce a fused protein with a short N- or C-terminal extension to facilitate subsequent purifications on columns or by use of antibodies. Alternatively, the protein of interest is purified by standard protein purification protocols. See for example PROTEIN PURIFICATION—PRINCIPLES AND PRACTICE, Springer Varlag publ., New-York; and PROTEIN BIOTECHNOLOGY, Humana Press, totowa, N.J.

The preparation of polyclonal antibodies is well-known to those skilled in the art. See, for example, Green et al., *Production of Polyclonal Antisera*, in IMMUNOCHEMICAL PROTOCOLS (Manson, ed.), pages 1-5 (Humana Press 1992); Coligan et al., *Production of Polyclonal Antisera in Rabbits, Rats, Mice and Hamsters*, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1-2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., *Purification of Immunoglobulin G (IgG)*, in METHODS IN MOLECULAR BIOLOGY, VOL. 10, pages 79-104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The invention provides a method for detecting myostatin or variants thereof in a subject predisposed to increased muscle mass which includes contacting an anti-myostatin antibody with a cell or protein and detecting binding to the antibody. An antibody which binds to myostatin polypeptide is labeled with a compound which allows detection of binding to myostatin. There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation. For purposes of the invention, an antibody specific for GDF-8 polypeptide may be used to detect the level of GDF-8 in biological fluids and tissues. Any specimen containing a detectable amount of antigen can be used. A preferred sample of this invention is muscle tissue. The level of GDF-8 in the suspect cell can be compared with the level in a normal cell to determine whether the subject is predisposed to a GDF-8-associated increase in muscle mass.

The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

The invention includes antibodies immunoreactive with GDF-8 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and $F(ab')_2$, Fv and SCA fragments which are capable of binding an epitopic determinant on GDF-8.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As is mentioned above, antigens that can be used in producing myostatin-specific antibodies include myostatin polypeptides or myostatin polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Kits for Detection of Myostatin

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

One of the container means may comprise a probe which is or can be detectably labeled. Such probe may be an antibody or nucleotide specific for a target protein, or fragments thereof, or a target nucleic acid, or fragment thereof, respectively, wherein the target is indicative, or correlates with, the presence of myostatin, or variants thereof. For example, oligonucleotide probes of the present invention can be included in a kit and used for examining the presence of myostatin variants, as well as the quantitative (relative) degree of binding of the probe for determining the occurrence of specific strongly binding (hybridizing) sequences, thus indicating the likelihood for an subject having or predisposed to having increased muscle mass. Thus, where the variant nucleotide sequence to be detected is myostatin, a hybridization probe can be utilized which is capable of hybridizing with nucleotide sequences comprising:

```
5'-GTGGAGTGTTCAT-3'  (SEQ ID NO:5);

5'-GATTCTGTCACAA-3'  (SEQ ID NO:6);

5'-AATTCACATTCTC-3'  (SEQ ID NO:7); or

5'-AATTCATATTCTC-3'  (SEQ ID NO:8)
``` and sequences complementary thereto. Exemplary oligonucleotide probes which hybridize to the target nucleic acid sequence include:

```
5'-ATGAACACTCCAC-3'  (SEQ ID NO:9);

5'-TTGTGACAGAATC-3'  (SEQ ID NO:10);

5'-GAGAATGTGAATT-3'  (SEQ ID NO:11); or

5'-GAGAATATGAATT-3'  (SEQ ID NO:12)
``` and sequences complementary thereto.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the target nucleic acid sequence, such as a myostatin variant nucleic acid sequence, this can be accomplished using oligonucleotide(s) that are primers for amplification. These oligonucleotide primers are based upon identification of the flanking regions contiguous with the target nucleotide sequence. For example, in the case of myostatin, these oligonucleotide primers comprise sequences which hybridize with nucleotide sequences flanking myostatin exon 3. Exemplary target sequences include the following nucleotide sequences:

```
                                              (SEQ ID NO:1)
5'-GATCCCAAAACACTCTCCTACCTCGGATCCGCG-3'; and (SEQ ID NO:2)
5'-CCCCTCAACAATTTTGAAACTGTGGGATCCGCG-3', and
``` sequences complementary thereto. Exemplary oligonucleotides which hybridize to such sequences include:

```
                                              (SEQ ID NO:3)
5'-CGCGGATCCGAGGTAGGAGAGTGTTTTGGGATC-3'; and (SEQ ID NO:4)
5'-CGCGGATCCCACAGTTTCAAAATTGTTGAGGGG-3'.
```

The kit may also contain a container containing antibodies which bind to a target protein, or fragments thereof, or variants of such a protein, or fragments thereof. Thus, a kit may contain antibodies which bind to wild-type myostatin or to myostatin variants. Such antibodies can be used to distinguish the presence of a particular myostatin variant or the level of expression of such variants in a specimen.

EXAMPLE 1

Cloning of Myostatin

Poly A-containing RNA was isolated from human (obtained from the International Institute for the Advancement of Medicine, Exton, Pa.), Holstein cow, sheep (Ruppersberger & Sons, Baltimore, Md.), pig (Bullock's Country Meats, Westminster, Md.), White Leghorn chicken (Truslow Farms, Chestertown, Md.), turkey (kindly provided by D. Boyer and D. Miller at Wampler Foods, Oxford, Pa.) and zebrafish (kindly provided by S. Fisher and M. Halpern) skeletal muscle tissue as described previously (Lee, S-J., *Mol. Endocrinol.* 4: 1034). cDNA libraries were constructed in the lambda ZAP II vector (Stratagene, La Jolla, Calif.) according to the instructions provided by the manufacturer and screened without amplification. Rat and baboon skeletal muscle cDNA libraries and a bovine (Holstein) genomic library were purchased from Stratagene. Library screening and analysis of clones were carried out as described (5) except that the final washes were carried out in 25 mM sodium phosphate pH 8.5, 0.5 M NaCl, 2 mM EDTA, 0.5% SDS at 65° C.

EXAMPLE 2

Sequencing of Bovine Genomic DNA

Blood from cattle was spun at 5,000 rpm for 15 min., resuspended in 150 mM NaCl, 100 mM EDTA, and digested with 200 μg ml$^{-1}$ proteinase K, 1% SDS at 44° C. Semen (Select Sires, Rocky Mount, Va.) was digested in 50 mM Tris pH 8.0, 20 mM EDTA, 1% sarcosyl, 0.2 M β-mercaptoethanol, 200 μg ml$^{-1}$ proteinase K. DNAs were purified on a CsCl gradient. Exon 3 was amplified by PCR from 1 μg genomic DNA using primer pairs 137ACM 5'-CGCG-GATCCGAGGTAGGAGAGTGTTTTGGGATC-3' (SEQ ID NO:3) and 138ACM 5'-CGCGGATCCCA-CAGTTTCAAAATTGTTGAGGGG-3' (SEQ ID NO:4) at 94° C. for 1 min., 52° C. for 2 min. and 72° C. for 2 min.

for 40 cycles. PCR products were digested with BamHI, subcloned into pBluescript and sequenced.

EXAMPLE 3

Southern Blot Analysis of Myostatin Variants

One-fifth of exon 3 amplification products were electrophoresed on 2% agarose gels, blotted to nylon membranes, hybridized with $^{32}$P-labeled 13-mers as described (Gärtner et al., *Nature Genetics* 1:16, 1992) and washed in 30 mM sodium citrate, 300 mM NaCl, 0.1% SDS. Primers used were 146 ACM 5'-ATGAACACTCCAC-3' (SEQ ID NO:9) (Holstein wild-type sequence, nucleotides 936-948), 145ACM 5'-TTGTGACAGAATC-3' (SEQ ID NO:10) (Belgian Blue mutation, nucleotides 931-936 with 948-954), 673SJL 5'-GAGAATGTGAATT-3' (SEQ ID NO: 11) (Holstein wild-type sequence, nucleotides 1050-1062) and 674SJL 5'-GAGAATATGAATT-3' (SEQ ID NO: 12) (Piedmontese mutation, G1056A).

EXAMPLE 4

Preparation of Antibodies Against GDF-8 and Expression of GDF-8 in Mammalian Cells In order to prepare antibodies against GDF-8, GDF-8 antigen was expressed as a fusion protein in bacteria. A portion of murine GDF-8 cDNA spanning amino acids 268-376 (mature region) was inserted into the pRSET vector (Invitrogen) such that the GDF-8 coding sequence was placed in frame with the initiating methionine codon present in the vector; the resulting construct created an open reading frame encoding a fusion protein with a molecular weight of approximately 16,600. The fusion construct was transformed into BL21 (DE3) (pLysS) cells, and expression of the fusion protein was induced by treatment with isopropyl-thio-β-galactoside as described (Rosenberg, et al., *Gene*, 56:125-135). The fusion protein was then purified by metal chelate chromatography according to the instructions provided by Invitrogen.

The purified fusion protein was used to immunize both rabbits and chickens. Immunization of rabbits was carried out by Spring Valley Labs (Sykesville, Md.), and immunization of chickens was carried out by HRP, Inc. (Denver, Pa.). Western analysis of sera both from immunized rabbits and from immunized chickens demonstrated the presence of antibodies directed against the fusion protein.

To express GDF-8 in mammalian cells, the murine GDF-8 cDNA sequence from nucleotides 48-1303 was cloned in both orientations downstream of the metallothionein I promoter in the pMSXND expression vector; this vector contains processing signals derived from SV40, a dihydrofolate reductase gene, and a gene conferring resistance to the antibiotic G418 (Lee and Nathans, *J. Biol. Chem.*, 263:3521-3527). The resulting constructs were transfected into Chinese hamster ovary cells, and stable tranfectants were selected in the presence of G418. Two milliliters of conditioned media prepared from the G418-resistant cells were dialyzed, lyophilized, electrophoresed under denaturing, reducing conditions, transferred to nitrocellulose, and incubated with anti-GDF-8 antibodies (described above) and [$^{125}$I]iodoproteinA.

EXAMPLE 5

Cloning of Myostatin Variants and Myostatin from Different Species

To clone the myostatin gene from other species, cDNA libraries were constructed from RNA isolated from skeletal muscle tissue and screened with a mouse myostatin probe corresponding to the mature, active portion of the molecule, the conserved carboxy-terminal region. An alignment of the predicted amino acid sequences of murine, rat, human, baboon, bovine, porcine, ovine, chicken, turkey and zebrafish myostatin deduced from nucleotide sequence analysis of full-length cDNA clones showed a putative signal sequence for secretion and a putative RxR proteolytic processing site (amino acids 263-266) followed by a region containing the conserved C-terminal cysteine residues found in all TGF-β family members (McPherron et al., (1996) in *Growth Factors and Cytokines in Health and Disease*, eds. LeRoith, D. & Bondy, C. (JAI Press, Greenwich, Conn.), Vol. 1B, pp. 357-393). This alignment showed that myostatin is highly conserved across species. In fact, the sequences of murine, rat, human, porcine, chicken and turkey myostatin are 100% identical in the C-terminal region following the putative proteolytic processing site, and baboon, bovine, and ovine myostatin contain only 1-3 amino acid differences in the mature protein. Zebrafish myostatin is considerably more diverged and is only 88% identical to the others in this region.

The high degree of sequence conservation of myostatin across species suggests that the function of myostatin has also been conserved. To determine whether myostatin plays a role in regulating muscle mass in animals other than mice, we investigated the possibility that mutations in the myostatin gene might account for the increased muscle mass observed in double muscled livestock breeds. Double muscling, which has been observed in many breeds of cattle for the past 190 years, appears to be inherited as a single major autosomal locus with several modifiers of phenotypic expression resulting in incomplete penetrance (Ménissier, F. (1982) in *Muscle Hypertrophy of Genetic Origin and Its Use to Improve Beef Production*, eds. King, J. W. B. & Ménissier, F. (Martinus Nijhoff, The Hague), pp. 387-428.). In the most extensively studied double muscled breed of cattle, Belgian Blue, the double muscling phenotype segregates as a single genetic locus designated muscular hypertrophy (mh) (Hanset et al., *Génét. Sél. Evol.* 17, 359, 1987). The mh mutation, which is partially recessive, causes an average increase in muscle mass of 20-25%, a decrease in mass of most other organs (Ansay et al., *Livest. Prod. Sci.* 6,:, 1979; Hanset, in *Breeding for Disease Resistance in Farm Animals*, ed. Owen, J. B. (C. A. B. International), pp.467-478, 1991) and a decrease in intramuscular fat and connective tissue (Hanset et al., in *Muscle Hypertrophy of Genetic Origin and Its Use to Improve Beef Production*, eds. King, J. W. B. & Ménissier, F. (Martinus Nijhoff, The Hague), pp. 341-349, 1982). The mh locus is tightly linked to markers on a region of bovine chromosome 2 (Charlier et al., *Mam. Genome* 6:788, 1995) that is syngenic to a region of human chromosome 2 (2q32) (Solinas-Toldo et al., *Genomics* 27:489, 1995) to which we had mapped the human myostatin gene by FISH.

Figure 1C:
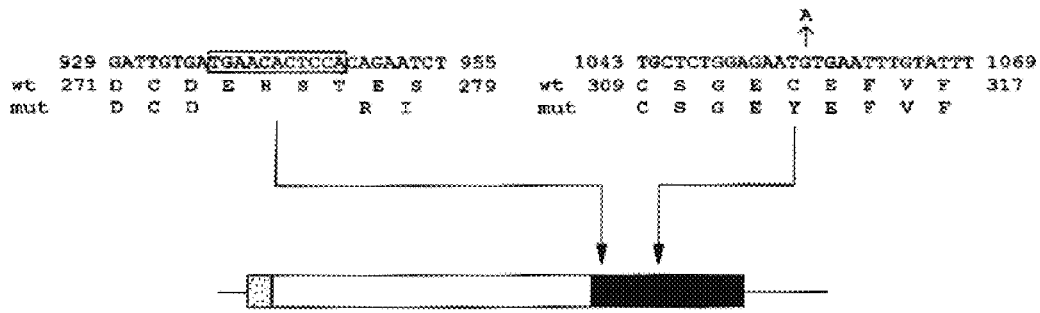
FIG. 1C shows partial nucleotide and amino acid sequences for Belgian Blue (SEQ ID NOS: 13 and 15, respectively) and Piedmontese (SEQ ID NOS: 16 and 18, respectively). The sequences are numbered relative to wild-type (SEQ ID NOS: 14 and 17, respectively). The Belgian Blue 11 nucleotide deletion (D937-947) is boxed and the Piedmontese G1056A transition is marked. Bold letters indicate nucleotide and amino acid changes. Arrows identify the locations of the mutations in the myostatin coding sequence. Shading indicates the signal sequence (gray), pro-region (white) and mature C-terminal region (black).
Figure 2:
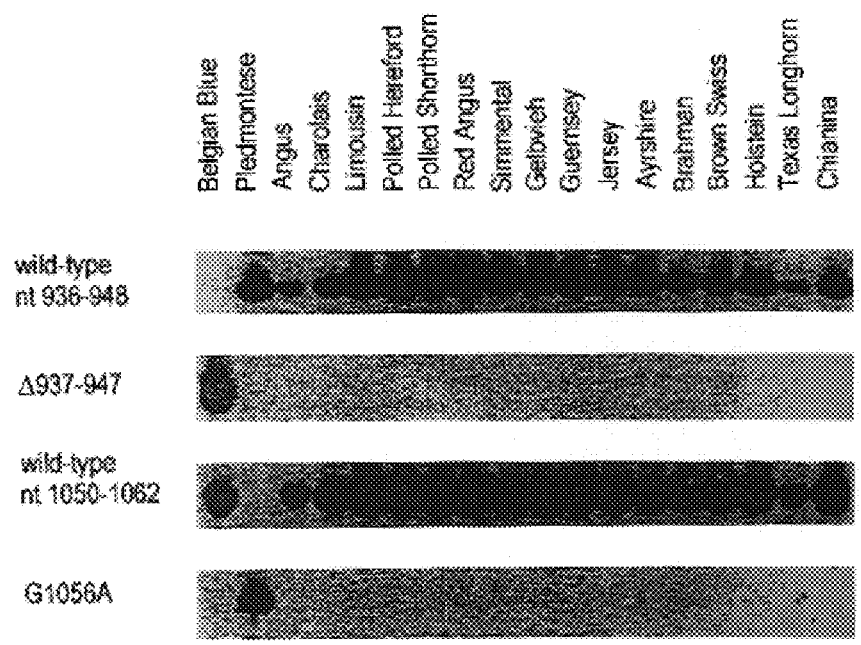
FIG. 2 is a Southern hybridization blot indicating the presence of the Belgian Blue and Piedmontese mutant sequences only in double-muscled breeds of cattle. Exon 3 PCR products hybridized to oligonucleotide probes spanning the wild-type sequence of the region of the Belgian Blue mutation (top row), the Belgian Blue mutation D937-947 (second row), the wild-type sequence at nucleotide 1056 (third row) and the Piedmontese mutant sequence at nucleotide 1056 (bottom row).

The similarities in phenotype between the myostatin null mice and the Belgian Blue cattle breed and the similar map positions of the myostatin gene and the mh locus suggested the bovine homolog of myostatin as a candidate gene for the mh locus. To determine whether the bovine myostatin gene is mutated in the Belgian Blue breed, all three exons of the gene from the full blood Belgian Blue bull were amplified by PCR, subcloned and sequenced. The Belgian Blue myostatin coding sequence was identical to the Holstein sequence except for a deletion of nucleotides 937-947 in the third exon (FIG. 1). This 11 nucleotide deletion causes a frame-shift that is predicted to result in a truncated protein that terminates 14 codons downstream of the site of the mutation. The deletion is expected to be a null mutation since it occurs after only the first 7 amino acids of the C-terminal region resulting in a loss of 102 amino acids (amino acids 274-375). This mutation is similar to the targeted mutation in myostatin null mice in which the entire region encoding the mature protein was deleted (McPherron et al., *Nature* 387:83, 1997). By Southern analysis using oligonucleotides corresponding to the wild-type or mutant sequence, this mutation was found in both alleles in 14/14 full blood Belgian Blue cattle examined.

The myostatin gene was also sequenced in another cattle breed in which double muscling occurs at an extremely high frequency, Piedmontese (Masoero et al., (1982) in *Muscle Hypertrophy of Genetic Origin and Its Use to Improve Beef Production*, eds. King, J. W. B. & Ménissier, F. (Martinus Nijhoff, The Hague), pp. 450-459). The Piedmontese sequence contained 2 nucleotide changes relative to the Holstein sequence. One was a C to A transversion in exon 1 resulting in a conservative substitution of leucine for phenylalanine (amino acid 94). The second was a G to A transition in exon 3 resulting in a cysteine to tyrosine substitution in the mature region of the protein (amino acid 313) (FIG. 1). By Southern analysis, this mutation was found in both alleles in 10/10 double muscled Piedmontese cattle examined. This mutation is likely to result in a complete or almost complete loss of function as this cysteine residue is invariant not only among all myostatin sequences but also among all known members of the TGF-β superfamily (McPherron et al., (1996) in *Growth Factors and Cytokines in Health and Disease*, eds. LeRoith, D. & Bondy, C. (JAI Press, Greenwich, Conn.), Vol. 1B, pp. 357-393). This cysteine residue is known to be one of the amino acids involved in forming the intramolecular cystine knot structure in members of this superfamily for which the three-dimensional structure is known (Daopin et al., *Science* 257:369, 1992; Schlunegger et al., *Nature* 358:430, 1992; Griffith et al., *Proc. Natl. Acad. Sci. USA*, 93:878, 1996; Mittl et al., *Prot. Science* 5:1261, 1996). Furthermore, when the corresponding cysteine in activin A (cysteine 44) was mutated to alanine, the mutant protein had only 2% of wild-type receptor binding and biological activity (Mason, A. J., *Mol. Endocrinol* 8:325, 1994).

The similar map positions of the myostatin gene and the mh locus and the identification of relatively severe mutations in the myostatin gene of two different double muscled cattle breeds suggest that these mutations are responsible for the double muscling phenotype. To further support this hypothesis, we analyzed DNA isolated from 120 individual full blood or purebred cattle in 16 other breeds which are not classified as double muscled (11 Angus, 11 Charolais, 10 Holstein, 10 Brown Swiss, 10 Polled Hereford, 10 Gelbvieh, 9 Simmental, 9 Jersey, 9 Guernsey, 9 Ayrshire, 7 Limousin, 4 Brahman, 4 Polled Shorthorn, 4 Red Angus, 2 Chianina, 1 Texas Longhorn) were analyzed for the presence of each of these mutations. By Southern analysis, the cysteine to tyrosine substitution present in the Piedmontese breed was not detected in any of the 120 individuals. The 11 nucleotide deletion present in the Belgian Blue breed was detected in one allele of a single Red Angus non-double muscled full blood bull. These results demonstrate that myostatin mutations that cause double muscling have occurred at least twice in cattle.

Finally, to rule out the presence of other myostatin mutations in non-double muscled breeds, we determined the complete sequence of the myostatin coding region of 11 of these breeds (Angus, Charolais, Brown Swiss, Polled Hereford, Gelbvieh, Guernsey, Ayrshire, Limousin, Brahman, Polled Shorthorn, Texas Longhorn). This analysis revealed only polymorphisms that were either silent changes in the coding sequences or were present in the introns and untranslated regions.

Unlike in mice, a myostatin null mutation in cattle causes a reduction in sizes of internal organs and only a modest increase in muscle mass (20-25% in the Belgian Blue breed as compared to 200-300% in myostatin-deficient mice). It is possible that cattle may be nearer to a maximal limit of muscle size after generations of selective breeding for large muscle mass, unlike mice, which have not been similarly selected. In this regard, even in cattle breeds that are not heavily muscled, the myostatin sequence contains two adjacent non-conservative amino acid differences (EG versus KE) in the C-terminal region compared to all other species examined. While the functional significance of these differences is unknown, it is possible that these two changes represent a partial loss-of-function allele that became fixed in the population during many years of cattle breeding.

For agricultural applications, there are some disadvantages to double muscled cattle, namely the reduction in female fertility, lower viability of offspring and delay in sexual maturation (Ménissier, F. (1982) in *Muscle Hypertrophy of Genetic Origin and Its Use to Improve Beef Production*, eds. King, J. W. B. & Ménissier, F. (Martinus Nijhoff, The Hague), pp. 23-53). At least in the Belgian Blue breed, however, the increased muscle mass and increased feed efficiency largely offset these drawbacks. The fact that a null mutation in the myostatin gene in cattle results in animals that are still viable and fertile and produce high-quality meat demonstrates the potential value of producing an increase in muscle mass in other meat animals such as sheep, pig, chicken, turkey and fish by disrupting myostatin function. Indeed, the high degree of sequence conservation in animals ranging from mammals to birds to fish suggests that the biological function of myostatin has been conserved widely throughout the animal kingdom.

It will be apparent to those skilled in the art that various modifications and variations can be made to the compositions and processes of this invention. Thus, it is intended that the present invention cover such modifications and variations, provided they come within the scope of the appended claims and their equivalents. Accordingly, the invention is limited only by the following claims.

What is claimed is:

1. A method for detecting the presence of a target myostatin variant nucleic acid sequence in a nucleic acid-containing specimen wherein the specimen is from Piedmontese having increased muscle mass or having a predisposition for increased muscle mass as compared to a bovine subject having a wild-type nucleic acid sequence, said method comprising detecting the presence of a target Piedmontese myostatin variant nucleotide sequence having a homozygous G1056A substitution, wherein the presence of the variant target nucleotide sequence is indicative of increased muscle mass or a predisposition for increased muscle mass.

2. The method of claim 1, further comprising amplifying the target variant nucleic acid prior to detecting.

3. The method of claim 2, wherein the amplification is by means of oligonucleotides which hybridize to flanking regions of the target nucleic acid.

4. The method of claim 3, wherein the nucleotide sequence of the flanking regions to which the oligonucleotides hybridize is:

```
                                        (SEQ ID NO:1)
5'-GATCCCAAAACACTCTCCTACCTCGGATCCGCG-3'; and (SEQ ID NO:2)
5'-CCCCTCAACAATTTTGAAACTGTGGGATCCGCG-3'.
```

5. The method of claim 4, wherein the oligonucleotides are:

```
5'-GATTCTGTCACAA-3'; and       (SEQ ID NO:6)

5'-AATTCATATTCTC-3'; and       (SEQ ID NO:8)
``` a second container containing a means for detecting hybridization of the probe with the target nucleic acid.

6. The method of claim 1, wherein the target nucleic acid is detected using a nucleic acid hybridization probe.

7. The method of claim 6, wherein the target nucleic acid to which the nucleic acid hybridization probe hybridizes is 5'-GATTCTGTCACAA-3'(SEQ ID NO:6).

8. The method of claim 6, wherein the nucleic acid hybridization probe is 5'-TTGTGACAGAATC-3'(SEQ ID NO:10).

9. The method claim 1, wherein the specimen is a food product.

10. A kit useful for the detection of a target nucleic acid sequence in a specimen from a subject having increased muscle mass as compared to a subject having a wild-type nucleic acid sequence or having a predisposition for increased muscle mass, wherein the presence of the target nucleic acid sequence in the specimen is indicative of having or predisposed to having increased muscle mass, the kit comprising one or more containers comprising a first container containing a nucleic acid hybridization probe, wherein the probe is 5'-TTGTGACAGAATC-3'(SEQ ID NO:10) or 5'-GAGAATATGAATT-3'(SEQ ID NO:12), and wherein the probe hybridizes to a target nucleic acid selected from: predisposed to having increased muscle mass, the kit comprising carrier means being compartmentalized to receive in close confinement therein one or more containers comprising a first container containing oligonucleotides which hybridize to the flanking regions of a target nucleic acid, wherein the oligonucleotides hybridize to a nucleic acid having a sequence of:

```
                                        (SEQ ID NO:1)
5'-GATCCCAAAACACTCTCCTACCTCGGATCCGCG-3'; and (SEQ ID NO:2)
5'-CCCCTCAACAATTTTGAAACTGTGGGATCCGCG-3'.
```

11. The kit of claim 10, further comprising an amplification polymerase and deoxyribonucleotide(s).

12. The kit of claim 10, wherein the detectable means is selected from the group consisting of enzymes, chemiluminescers, radionuclides, fluorescent compounds, heavy metals and ligands.

13. The kit of claim 10, further comprising a third container containing oligonucleotides which hybridize to the flanking regions of a target nucleic acid, wherein the oligonucleotides hybridize to a nucleic acid having a sequence of:

```
                                        (SEQ ID NO:1)
5'-GATCCCAAAACACTCTCCTACCTCGGATCCGCG-3'; or (SEQ ID NO:2)
5'-CCCCTCAACAATTTTGAAACTGTGGGATCCGCG-3'.
```

14. The kit of claim 10, further comprising a third container containing oligonucleotides which hybridize to the flanking regions of a target nucleic acid, wherein the oligonucleotides are:

```
                                        (SEQ ID NO:3)
5'-CGCGGATCCGAGGTAGGAGAGTGTTTTGGGATC-3'; and (SEQ ID NO:4)
5'-CGCGGATCCCACAGTTTCAAAATTGTTGAGGGG-3'.
```

15. A kit useful for the detection of a target nucleic acid sequence in a specimen from a subject having increased muscle mass as compared to a subject having a wild-type nucleic acid sequence or having a predisposition for increased muscle mass, wherein the presence of the target nucleic acid sequence in the specimen is indicative of having or

```
                                        (SEQ ID NO:3)
5'-CGCGGATCCGAGGTAGGAGAGTGTTTTGGGATC-3'; and (SEQ ID NO:4)
5'-CGCGGATCCCACAGTTTCAAAATTGTTGAGGGG-3'.
```

16. The kit of claim 15, wherein the oligonucleotides are:

```
                                        (SEQ ID NO:3)
5'-CGCGGATCCGAGGTAGGAGAGTGTTTTGGGATC-3'; and (SEQ ID NO:4)
5'-CGCGGATCCCACAGTTTCAAAATTGTTGAGGGG-3'.
```

17. The method of claim 1, wherein the specimen is muscle tissue.

18. The method of claim 17, wherein the tissue is skeletal muscle tissue.

19. A method for detecting the presence of a target myostatin variant nucleic acid sequence in a nucleic acid-containing specimen wherein the specimen is from Belgian Blue having increased muscle mass or having a predisposition for increased muscle mass as compared to a bovine subject having a wild-type nucleic acid sequence, said method comprising detecting the presence of a target Belgian Blue myostatin variant nucleotide sequence having a homozygous deletion of nucleotides 937-947 in the 3rd exon, wherein the presence of the variant target nucleotide sequence is indicative of increased muscle mass or a predisposition for increased muscle mass.

20. The method of claim 19, further comprising amplifying the target variant nucleic acid prior to detecting.

21. The method of claim 20, wherein the amplification is by means of oligonucleotides which hybridize to flanking regions of the target nucleic acid.

22. The method of claim 21, wherein the nucleotide sequence of the flanking regions to which the oligonucleotides hybridize is:

```
5'-GATCCCAAAACACTCTCCTACCTCGGATCCGCG-3'; and    (SEQ ID NO:1)

5'-CCCCTCAACAATTTTGAAACTGTGGGATCCGCG-3'.        (SEQ ID NO:2)
```

23. The method of claim 22, wherein the oligonucleotides are:

```
5'-CGCGGATCCGAGGTAGGAGAGTGTTTTGGGATC-3'; and    (SEQ ID NO:3)

5'-CGCGGATCCCACAGTTTCAAAATTGTTGAGGGG-3'.        (SEQ ID NO:4)
```

24. The method of claim 19, wherein the target nucleic acid is detected using a nucleic acid hybridization probe.

25. The method of claim 24, wherein the target nucleic acid to which the nucleic acid hybridization probe hybridizes is:

```
5'-GATTCTGTCACAA-3'; or    (SEQ ID NO:6)

5'-AATTCATATTCTC-3'.       (SEQ ID NO:8)
```

26. The method of claim 24, wherein the nucleic acid hybridization probe is:

```
5'-TTGTGACAGAATC-3'; or    (SEQ ID NO:10)

5'-GAGAATATGAATT-3'.       (SEQ ID NO:12)
```

27. The method of claim 19, wherein the specimen is muscle tissue.

28. The method of claim 27, wherein the tissue is skeletal muscle tissue.

* * * * *